United States Patent [19]

Glowacki et al.

[11] Patent Number: 5,656,492
[45] Date of Patent: Aug. 12, 1997

[54] CELL INDUCTION DEVICE

[75] Inventors: Julie Glowacki, Jamaica Plain; Shuichi Mizuno, Brookline, both of Mass.

[73] Assignee: Brigham and Women's Hospital, Inc., Boston, Mass.

[21] Appl. No.: 17,281

[22] Filed: Feb. 12, 1993

[51] Int. Cl.⁶ ................................................. C12M 3/00
[52] U.S. Cl. .................... 435/284.1; 435/283.1; 435/402; 424/425; 424/484
[58] Field of Search .............. 435/240.1, 240.2, 435/240.21, 240.243, 284, 287, 283.1, 284.1; 424/484, 422–425; 229/72, 5.6

[56] References Cited

U.S. PATENT DOCUMENTS

| | | | |
|---|---|---|---|
| 2,189,273 | 2/1940 | Shomaker | 229/72 |
| 4,382,348 | 5/1983 | Kitsu et al. | 47/59 |
| 4,440,750 | 4/1984 | Glowacki et al. | 424/95 |
| 4,479,769 | 10/1984 | Kallok | 424/424 |
| 4,495,288 | 1/1985 | Jarvis, Jr. et al. | 435/241 |
| 4,546,083 | 10/1985 | Meyers et al. | 435/240 |
| 4,559,299 | 12/1985 | Rotman | 435/29 |
| 4,565,580 | 1/1986 | Miyata et al. | 106/124 |
| 4,565,784 | 1/1986 | Franzblau et al. | 435/240 |
| 4,601,893 | 7/1986 | Cardinal | 424/424 |
| 4,835,102 | 5/1989 | Bell et al. | 435/29 |
| 4,996,154 | 2/1991 | Gabriels, Jr. | 435/240 |
| 5,015,584 | 5/1991 | Brysk | 435/1 |
| 5,024,841 | 6/1991 | Chu et al. | 424/422 |
| 5,032,508 | 7/1991 | Naughton et al. | 435/32 |
| 5,108,753 | 4/1992 | Kuberasampath et al. | 424/422 |

FOREIGN PATENT DOCUMENTS

| | | |
|---|---|---|
| 0403650 | 12/1990 | European Pat. Off. . |
| 0421211 | 4/1991 | European Pat. Off. . |
| 0531631 | 3/1993 | European Pat. Off. . |
| 2054446 | 5/1972 | Germany . |
| 8304177 | 12/1983 | WIPO . |
| WO-A-9005179 | 5/1990 | WIPO . |
| WO-A-9101720 | 2/1991 | WIPO . |

OTHER PUBLICATIONS

Mizuno et al., "A Collagen/DBP Sponge System Designed for In Vitro Analysis of Chondroinduction", Dec. 4, 1991, Materials Research Society Symposium Proceedings, Tissue–Inducing Biomaterials, vol. 252.

Advertisement for Cellagen Membranes offered by ICN Biomedicals, Inc., Biochemicals Div. of Cleveland, OH.

A Collagen/DBP Sponge System Designed For IN VITRO Analysis Of Chonodroinduction, Mizuno et al. Orthopedic Research, Brigham and Women's Hospital, Harvard Medical School, Boston.

*Primary Examiner*—Milton Cano
*Attorney, Agent, or Firm*—Wolf, Greenfield & Sacks, P.C.

[57] ABSTRACT

The present invention features a device and method for inducing cell differentiation. One embodiment of the present invention features a device comprising a wall having an interior surface and an exterior surface. The interior surface defines a chamber. The exterior surface is capable of being placed in contact with biological tissues. The wall has an opening in communication with the chamber for receiving an induction material and for closing the chamber to contain the induction material. The wall comprises a biologically compatible, permeable material capable of receiving cells capable of differentiation. The device is used to contain an induction material in a biological environment and receiving cells in the chamber. The cells are allowed to differentiate in the presence of the induction material.

36 Claims, 1 Drawing Sheet

CELL INDUCTION DEVICE

This work was sponsored in part by National Institutes of Health Grant #CA 45548 to JG. The U.S. Government may have certain rights to this invention.

BACKGROUND OF THE INVENTION

Transdifferentiation or induction occurs when cells of one phenotype are transformed, in the presence of one or more growth and differentiation factors, into cells of another phenotype. One example is the response of connective tissue to demineralized bone powder. In the presence of demineralized bone powder, connective tissue cells are converted to chondroblasts, and produce a cartilage matrix that is resorbed and replaced by bone.

Devices used for the study of transdifferentiation have often relied upon semipermeable membranes as a support for the required growth and differentiation factor(s) and for the cells that are acted upon by these factors. These semipermeable membranes often induce an inflammatory response in a subject when implanted in vivo. Moreover, in vivo assays designed to test the ability of growth and differentiation factors, and other molecules that modulate this activity, are often expensive, cumbersome, and time-consuming. Furthermore, prior culture devices have suffered from problems associated with dispersion of growth and differentiation factors on the surface of a support. The factors are ineffective because the levels in the support are too low to cause the desired effect. As a result, in vitro systems for promoting transdifferentiation and and in vivo implants designed to induce transdifferention have been generally ineffective.

SUMMARY OF THE INVENTION

The present invention features a device and method for inducing cell differentiation. One embodiment of the present invention features a device comprising a wall having an interior surface and an exterior surface. The interior surface defines a chamber. The exterior surface is capable of being placed in contact with biological tissues. The wall has an opening in communication with the chamber for receiving an induction material and for closing the chamber to contain the induction material. The wall comprises a biologically compatible, permeable material capable of receiving cells capable of differentiation. The device is used to contain an induction material in a biological environment and receiving cells in the chamber. The cells are allowed to differentiate in the presence of the induction material.

In one preferred embodiment of the device the wall and opening comprise a first wall section and a second wall section. The first wall section has a chamber area for receiving an induction material and a peripheral edge area. The second wall section has a cooperating peripheral edge area capable of being received by the peripheral edge area of the first wall section to form the chamber.

One embodiment of the present device features a support. The support engages the peripheral edge areas of the first and second wall sections to provide closure of the edge areas and to facilitate handling. Preferably, the support comprises a housing. The housing has an inner surface and an outer surface. The inner surface defines a cavity having a groove for engaging the first and second wall sections. Preferably, the groove is defined by cooperating flanges projecting inwardly in spaced relationship.

Preferably, the housing has two ends. At least one end has a planar edge to allow the housing to stably rest on flat surfaces. The housing has conduits extending from the outer surface to the inner surface to allow the cavity to be in fluid communication with the environment at the outer surface when the housing is resting on the planar edge.

The edge opposite said planar edge is open to allow cells and other materials to be placed on the exterior surface of the wall.

One cell induction device of the present invention comprises a laminate including first and second layers of a structural matrix material. Each of the layers has an exterior and an interior peripheral surface. The interior peripheral surfaces of each of the first and second layers are engaged with each other in facing relationship. Engagement of the interior peripheral surfaces in this way defines a chamber between the two layers. The chamber is substantially free of structural matrix material. The engaged peripheral surfaces define a seam extending around the outer periphery of the laminate.

A substrate capable of inducing growth and/or differentiation of one or more cells is disposed within the chamber in an amount sufficient to optimize the density of substrate within the chamber. The laminate is preferably permeable and biocompatible with the substrate.

The substrate is preferably a material that is capable of inducing transdifferentiation of one or more cells. Most preferably, the substrate is an osteogenic material. In particularly preferred embodiments of the invention, the substrate is demineralized bone powder and the structural matrix is a structural protein such as collagen.

The cell induction device can further include a support for the laminate, this support being engaged with the peripheral seam of the laminate. The supporting structure is an annular collar having opposed ends, the peripheral seam of the laminate being attached to the inner peripheral surface of the annular collar. Most preferably, the laminate seam is attached between the opposed ends of the collar. One end of the collar includes a plurality of conduits for transferring culture media (i.e. cells to be cultured such as connective tissue) into the interior of the collar.

The invention includes a device for implanting into a subject. The device comprises a laminate including first and second layers of a permeable structural matrix. Each of the layers has an exterior and interior peripheral surface, the interior peripheral surfaces of said first and second layers are engaged together in facing relationship, defining a substantially hollow chamber that lacks the structural matrix. A substrate is disposed within the chamber, the substrate having inducing activity towards one or more cells that come in contact with the laminate. A plurality of induced cells is engaged with the laminate, some of said cells having been induced prior to implantation of the device.

The invention also pertains to a method for analyzing the inductive activity of cells. The method includes the step of providing a laminate including first and second layers of structural matrix material, each of the layers having an exterior and interior peripheral surface. The interior peripheral surfaces of the first and second layers are engaged in facing relationship to each other to define a substantially hollow chamber that is substantially free of the matrix. A substrate is disposed within the chamber and the substrate is allowed to contact cells that are capable being induced in the presence of the substrate. The laminate is incubated in the presence of these cells for time sufficient for the cells to be induced by the substrate (i.e. to grow and/or differentiate). The method also can include adding at least one cell growth factor and/or one glycosoaminoglycan to the laminate. Preferably, the substrate is demineralized bone powder.

The invention also pertains to methods of forming the device of the present invention. The method includes the steps of providing a mold comprising a tube having opposed ends. A first solution of structural matrix material is deposited into the bottom of the tube mold and frozen. A spacer is placed on top of the frozen matrix, but allowing a small uncovered peripheral edge of the matrix to remain exposed. The spacer and matrix are again frozen and a second amount of structural matrix material deposited on top of the spacer. A second spacer is placed over the second structural matrix material and the entire mold is lyophilized. After lyophilization, the spacers are carefully removed from the structural matrix to produce a laminate including first and second layers, each of the layers having exterior and interior peripheral surfaces. The spacers prevent formation of a denser, impermeable layer over the laminate. The interior peripheral surfaces of each of the layers sheets are engaged in facing relationship to define a peripheral seam. The laminate further defines a hollow chamber that is substantially free of the structural matrix material. A substrate is disposed between the layers of the laminate. Optionally, the laminate containing the substrate is engaged with a support by engaging the peripheral seam of the laminate with a receiving means in the support.

DETAILED DESCRIPTION OF THE INVENTION

The present invention involves a three-dimensional laminate and its use as the framework for a three-dimensional, cell induction device. This device simulates physiologic conditions found in vivo to a greater degree than previously described systems. The device is applicable to the growth of different types of cells and to the formation of a number of different tissues, including but not limited to bone, and connective tissue.

The device has a variety of applications. For example, the device may be transplanted from an in vitro situation to a living organism in vivo or implanted directly into a living organism. Alternatively, proliferating cells can be isolated from the device for transplantation. The device may also be used in vitro for cytotoxicity testing and screening compounds. In yet another application, the device may be used as a "bioreactor" to produce cellular products in quantity.

In accordance with the invention, a substrate capable of promoting induction of one or more target cells is disposed into a chamber of a preestablished, three-dimensional laminate structure. The term "induction" refers to the growth and/or differentiation of a target cell; in particular the term "inductive" refers to substrates capable of promoting trans-differentiation processes such as, for example, the phenotypic transformation of mesenchyme cells (e.g., fibroblasts) into cartilage-producing chondroblasts.

The chamber is formed by a three-dimensional laminate with or without additional cells and/or elements, described more fully herein. Materials of the laminate can support the growth of many different cells and tissues in the three-dimensional culture system. Once formed, the substrate is disposed within the three-dimensional laminate. Other growth and regulatory factors may also be added to the laminate.

Figure 1:
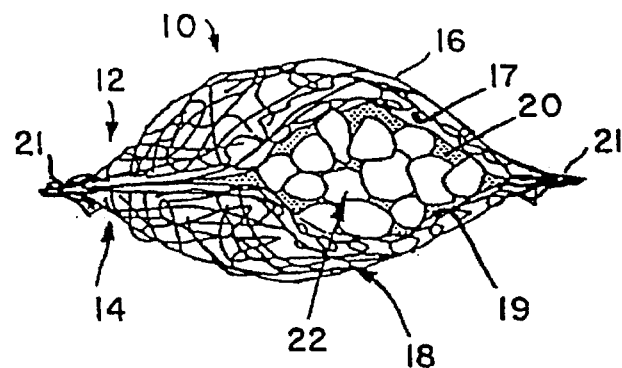
FIG. 1 is a schematic, cross-sectional view of the laminate of the invention.

Referring to FIG. 1, a laminate of the invention is shown. The laminate 10 includes first 12 and second 14 layers of structural matrix material. The term "matrix" means a material that can be visually homogenous, but preferably is granulated, fibrillar and/or filamentous in structure. Each of the first and second layers has an exterior peripheral surface, 16, 18 respectively. Each of the layers has interior peripheral surfaces, 17, 19, respectively. The interior peripheral surfaces 17, 19 of the first and second layers are engaged together in facing relationship to form a seam 21. The seam 21 extends substantially around the entire periphery of the laminate.

A substantially hollow chamber 20 is defined between surfaces 17 and 19 and chamber 20 is substantially free of the structural matrix material. A substrate 22 is disposed within chamber 20. The substrate 22 is capable of inducing growth and/or differentiation of one or more cells (not shown).

The structural matrix of the invention is permeable to the environment of use. By "permeable" it is meant that the laminate will allow ingress and egress of materials (e.g. target cells, target cell fragment, blood vessels, bodily fluids) without restricting these materials to any particular molecular weight or size. This property is to be distinguished from well-known semipermeable or selectively permeable membranes that discriminate according to molecular weight and/or size. The permeable nature of the present laminates fosters the development of a microenvironment within the laminate that simulates in vivo conditions.

The laminate of the present invention must also be biocompatible with the substrate. Conventional cell culture devices, particularly if they are implanted in vivo, are typically implants in which cells or cellular products are released from the implant to act on a distant target. The biocompatability of these structures is tested by assaying the implants for the presence of inflammatory cells (i.e. foam cells, polymorphonuclear leukocytes, macrophages, and the like) after 7 days. If the assay is negative (i.e. no inflammatory cells are present in the implant), the implant material is considered biocompatible.

In contrast, the present laminates require target cells to be induced within the laminate itself so that the action of the substrate on the target cells is not at a distance. The meaning of the term "biocompatible", in the present context, is stricter and refers to the ability of the laminate to maintain the biological integrity of the substrate. Thus, a biocompatible laminate must: (i) not directly inhibit the substrate's ability to attract structures such as, for example, blood vessels, or to induce one or more cells; and/or (ii) prevent inflammatory cells from compromising the substrate's ability to attract or induce one or more cells. In particular, preferred laminates of the invention are considered biocompatible with a substrate if a transient infiltrate of polymorphonuclear leukocytes is not observed after 2 days in vivo.

The in vivo biocompatability of a given laminate can be easily tested by preparing the laminate and the enclosed substrate and histologically examining the laminate for the presence of inflammatory cells and correlating the histological examination with assays of inductive activity.

Disposition of the substrate inside the hollow chamber will sustain active proliferation and differentiation of cells in culture for much longer time periods than will homogeneous dispersion of substrate throughout the structural matrix material itself. Although the applicants are under no duty or obligation to explain the mechanism by which the invention works, a number of factors inherent in the three-dimensional culture may contribute to this:

(a) The chamber allows for a biomimetic spatial distribution of substrate (i.e. a substrate distribution analogous to that found in the counterpart tissue in vivo).

(b) The increase in potential volume for particulate substrates in the chamber may allow the establishment of a particulate substrate packing density conducive to growth and/or differentiation of cells. That is, it is believed that the disposition of particulate substrates within the chamber optimizes cell-substrate interactions by allowing greater packing of cells and substrate in the chamber.

(c) It has been recognized that maintenance of a differentiated cellular phenotype requires a favorable microenvironment for production of growth/differentiation factors. It is believed that the present device provides this microenvironment suitable for appropriate cellular interactions.

(d) The laminate lacks any impermeable portions that would prevent infiltration of fluids, cells, or other structures (e.g. blood vessels) into the chamber.

The laminate matrix may be of any material: (a) that allows cells to attach to it (or can be modified to allow cells to attach to it); and (b) can be formed as a plurality of layers whose interior peripheral surfaces can naturally seal or anneal themselves together in facing relationship without use of adhesives, excipients, or other added materials, thus defining a chamber.

A number of materials are suitable for the laminates of the present invention. The preferred laminates should:

(i) have a pH in vivo near, or above neutrality (between about 7.0 to about 8.0). This property tends to exclude bioerodible polymers such as polyglycolides or polylactides, because they appear to be acidic when implanted in vivo. The acidity of these polymers prevents migration of fibroblasts and differentiation into cartilage inside the laminates;

(ii) be permeable, rather than semipermeable and/or selectively permeable;

(iii) be biocompatible with the substrate in vitro and in vivo.

A number of permeable materials may be used to form the matrix, including but not limited to: minerals (e.g. hydroxyapatite, aragonite), ceramics, glasses, dacron (poll;esters), polytetrafluorothylene (PTFE; TEFLON), nitrocellulose, cotton, cellulose, gelatin, dextran, etc. Provided that they meet the requirements set out above, any of these materials may be fabricated into a laminate.

However, the most preferred materials for forming the laminate of the invention are structural proteins such as elastin fibers, fibronectin, laminin and the like. Particularly preferred materials for forming the laminate are collagens that have been treated so that they maintain porosity upon lyophilization and are not inflammatory in vivo.

There are five types of collagen known: Type I, found in fibroblasts, bone, dentin and connective tissue; Type II, found in hyaline and elastic cartilage; Type III, found in blood vessels; Type IV, found in basement membranes; and Type V, found in bone, smooth muscle and fetal membranes. Type I is preferred for the laminate of the present invention.

A substrate capable of inducing growth and/or differentiation of one or more cells, with or without other cells and elements described below, is disposed into the chamber. The substrate may be derived from cells or tissues which can be obtained by biopsy (where appropriate) or upon autopsy. The substrate is a material which can induce growth and/or differentiation of one or more cell types. General substrates of this category include, but are not limited to: (i) osteogenic; (ii) angiogenic; (iii) adipogenic; or (iv) hematopoietic substrates. Specific substrates that have these respective characteristics include: (i) demineralized bone powder (DBP)-capable of inducing, for example, mesenchyme cells such as fibroblasts, to form chondroblasts; (ii) heparan sulfate-capable of inducing blood vessel formation; (iii) steroid-producing cells-capable of converting fibroblasts to adipose tissue; and (iv) extracellular matrix of bone marrow connective tissue cells-capable of converting target cells into blood cells.

The substrate has a concentration chosen to optimize its packing density in the chamber. The packing density of the substrate is important in determining its inducing ability. Differentiation of fibroblasts into chondroblasts often occurs between adjacent particles of DBP. For a laminate about ⅜" in diameter, about 10 mg of DBP is optimal. Those of ordinary skill in the art can readily determine the optimum amount of other substrates by assaying the relationship between substrate amount and the inducing ability of that substrate. In the case of DBP, packing density is optimized visually by making sure that each DBP particle is in physical contact with an adjacent DBP particle.

In addition to the substrate, other materials may be added to the laminate to support long term growth and/or differentiation in culture. For example, cells found in loose connective tissue may be inoculated into the laminate. Such cells include, but are not limited to endothelial cells, pericytes, macrophages, monocytes, plasma cells, mast cells, adipocytes, osteoblasts, and bone marrow stromal cells. These cells may readily be derived from appropriate organs such as skin, liver etc., using methods known in the art. Other cells can include prokaryotic cells, eukaryotic cells, and recombinantly engineered cells.

The growth of cells in the presence of the substrate may be further enhanced by adding to the laminate glycoproteins (such as, for example, bone morphogenic protein), glycosaminoglycans (e.g., heparan sulfate, chondroitin-4-sulfate, chondroitin-6-sulfate, dermatan sulfate, keratan sulfate, etc.) cellular matrix, and/or other materials. The addition of growth factors may be used to enhance, alter, or modulate proliferation and cell maturation in the cultures. The growth and activity of cells in culture can be affected by a variety of growth factors such as platelet-derived growth factor (PDGF), transforming growth factor-beta (TGF-beta), insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include steroids prostaglandins, interleukins, vitamins, and naturally-occurring chalones. For example, transdifferentiation of fibroblasts or bone marrow cells can be modulated by steroids so that the fibroblasts or bone marrow is transformed into adipocytes, instead of chondrocytes.

After disposition of the substrate into the chamber formed by the laminate, the laminate is incubated in an appropriate nutrient medium containing one or more cells capable of growth and/or differentiation under the influence of the substrate. Many commercially available media such as RPMI 1640, Fisher's, Iscove's, McCoy's, and the like may be suitable for use. The laminate can be suspended or floated in the medium during the incubation period in order to maximize proliferative and/or differentiation activity. In addition, the culture should be fed periodically to remove the spent media, depopulate released cells, and add fresh media.

A wide variety of cells can be introduced into the laminate, depending upon the particular substrate disposed within the chamber. For example, if DBP is the enclosed substrate, fibroblasts are prepared and added to the laminate. Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase and/or hyaluronidase, DNase, pronase, dispase etc. Mechanical disruption can also be accomplished by a number of methods including, but not limited to the use of grinders, blenders sieves, homogenizers, pressure cells, or insonators to name but a few. For a review of tissue disaggregation techniques, see Freshney, *Culture of Animal Cells*, A Manual of Basic Technique, 2d Ed., A. R. Liss, Inc. New York, 1987, Ch. 9, pp. 107–126.

Figure 2:
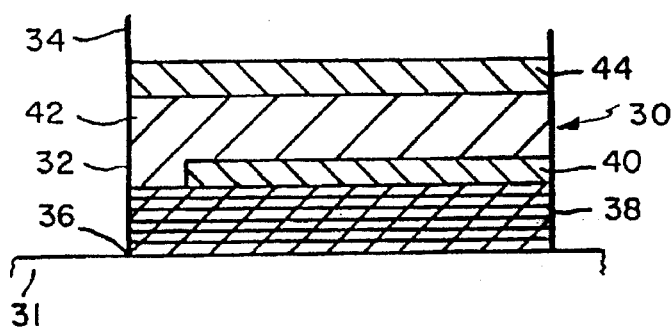
FIG. 2 is a schematic, cross-sectional view of a method and apparatus for making the laminate of the invention.

A unique feature of the present invention is the manner and apparatus used to fabricate the laminated cell culture device of the invention. A mold made of an inert elastomer (i.e. Tygon® tubing) is provided. FIG. 2 illustrates a preferred mold and laminate in an intermediate step in the manufacturing process. The mold 30 is a substantially annular collar 32 having opposed ends 34, 36. To make the mold, ⅜" TYGON® tubing is cut into approximately 1 cm pieces. One end 36 of the tube is closed off by gluing the tube on a tissue culture dish 31 with, for example, Medical Adhesive Silicon (Dow Corning). The molds are dried.

A preferred laminate is formed by providing a first solution 38 (up to several hundred microliters) of structural protein (i.e. a collagen matrix) to the closed end 36 of mold 30. Between 80–200 microliters of structural protein solution is optimal for the preferred laminate structures of the invention.

The mold is then frozen. A spacer 40 (preferably wet paper) is placed on top of the frozen matrix 38, but the peripheral edges of the matrix remain exposed. The spacer 40 and matrix 38 are again frozen and a second amount of structural protein matrix 42 (up to several hundred microliters) deposited on top of spacer 40. A second spacer 44 is placed over the second structural protein matrix 42. The peripheral edges of the second matrix do not need to remain exposed. The entire mold is lyophilized.

After lyophilization, the spacers are carefully removed from the structural protein matrix. The interior peripheral surfaces of the layers spontaneously seal or otherwise anneal together during the lyophilization procedure to form a seam, defining a substantially hollow chamber that is substantially free of the structural matrix material. This seam extends substantially around the entire outer periphery of the laminate (See FIG. 1). The use of the spacers eliminates development of an impermeable, dense shell of protein that typically forms during lyophilization. Lyophilization provides enough strength to the laminate to allow for ease of handling and packing of the laminate.

After the laminate is formed, the chamber is packed with the substrate. A preferred substrate is demineralized bone powder, prepared from cortical sections of femoral and tibial bones (i.e. rat) (See Example 1). The bone is extracted with an alcohol solvent (i.e. ethanol) and an ether solvent. The dehydrated bone is frozen and pulverized in, for example, a liquid nitrogen impacting mill (Spex Industries, Metuchen, N.J.). Bone pieces are seived and collected, preferably as a fraction between 75 and 250 um. Mineral extraction is performed with acid (i.e. 0.5 HCl) for several hours at room temperature. Final drying is achieved by solvent washing, as above.

Optionally, the laminate containing the substrate is secured to a support device. The support device is substantially identical to the manufacturing mold with the addition of several features.

Figure 3:
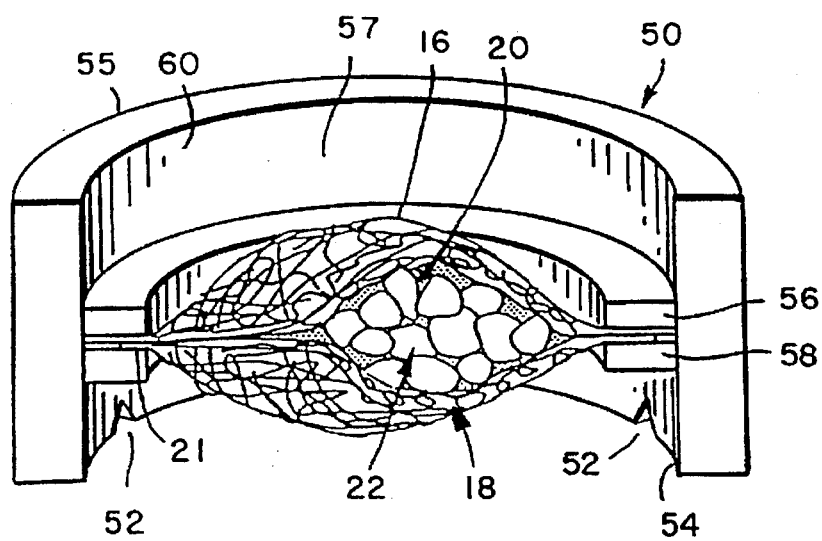
FIG. 3 is a schematic, cross-sectional view of the laminate of the invention engaged with a support device.

FIG. 3 illustrates a support 50 after the substrate 22 has been disposed into chamber 20. A plurality of conduits 52 has been cut into one end 54 of ⅜" TYGON tubing. The conduits provide for entry of culture fluid from outside the support. The opposed end 55 of support 50 receives the target cells (not shown) and the space 57 defined by laminate's peripheral surface 16, the inner periphery 60 of the support 50, and end 55, preferably serves as a receptacle for target cells so that they may infiltrate and migrate into the laminate.

A pair of opposed flanges 56, 58 or silicon O-rings is placed on the inner periphery 60 of support 50. The flanges 56,58 are in facing relationship to each other. The opposed flanges on the inner periphery 60 of the support 50 receives the peripheral seam 21 of the laminate. Silicon tubing (about ⅜" in diameter, 1/16" wall thickness, 1.5 mm in length) is preferably used to make the flanges. The silicon tubing is fit in place on the inner periphery 60 of support 50.

The support containing the laminate packed with substrate can be used in the preliminary stages of in vitro cell culture to provide a stable receptacle and platform for the migration, growth, and differentiation of one or more cells. It will be understood that a variety of other laminate configurations can be fabricated using the present methods. For example, a multichamber laminate can be easily fabricated using several spacers and more than two layers of structural matrix material. Each chamber can be charged with the same, or different, substrate.

The device of the invention can be used in a variety of applications. These include, but are not limited to, transplantation or implantation of the laminate in vivo; screening differentiation inducing factors, cytotoxic compounds, allergens, growth/regulatory factors, pharmaceutical compounds, etc., in vitro; studying the mechanism by which drugs and/or growth factors operate; and the production of biologically active products, to name but a few.

For transplantation or implantation in vivo into a subject (i.e. an animal, preferably a mammal such as a human), either the cells obtained from the laminate or the entire laminate could be implanted, depending upon the type of tissue involved. For example, three-dimensional bone cultures can be maintained in vitro for long periods; the cells isolated from these cultures can be used in transplantation or the entire laminate may be implanted.

Three-dimensional tissue culture implants may, according to the invention, be used to replace or augment existing tissue, to introduce new or altered tissue, to modify artificial prostheses, or to join together biological tissues or structures. For example, and not by way of limitation, specific embodiments of the invention would include (i) removal of cells from a subject (i.e. fibroblasts from a human skin biopsy sample), in vitro induction of these cells to form chondroblasts, and production of three-dimensional bone culture implants used in vivo in the same subject to replace bone destroyed during chemotherapeutic treatment; (ii) genetically altering cells grown in three-dimensional culture, for example to produce three-dimensional cultures of chondroblasts which express a recombinant gene encoding a therapeutic agent, and their use in vivo to replace bone destroyed during chemotherapeutic treatment.

The device may be used in vitro to screen a wide variety of putative substrates and growth/regulatory factors. To this end, cell cultures are maintained in vitro and exposed to a particular substrate suspected of having inducing activity. Response of the cell culture is assayed using conventional methods (see, Example 1). The ability of compounds to modulate (i.e. enhance or suppress) inductive activity can also be measured by, for example, vital staining techniques or by analyzing the cellular contents of the laminate e.g., by total cell counts, and differential cell counts. This may be accomplished using standard cytological, biochemical and/or histological techniques, including the use of immunocytochemical techniques employing antibodies that define type-specific cellular antigens. The effect of various drugs on cells cultured in the device may also be assessed. For example, drugs that increase bone and/or cartilage formation can be tested on chondroblast cultures.

The device of the invention can also be used to study and assess the biocompatability of various structural matrix materials. Laminates can be fabricated of the material to be tested and the laminate charged with a particular substrate. The effect of different laminate materials on the inductive capacity of the substrate can be assayed using the methods described herein.

The device of the invention may be used as a model system for the study of physiologic or pathologic conditions. For example, in a specific embodiment of the invention, a laminate may be used as a model for a bone system can be used to study the penetration of substances through bone, and/or as a model system to study the effect of bone transdifferentiation factors.

Depending upon the intended use for the proliferated and/or differentiated cells, various specialized cells may be added to the device. For example, the long-term growth of bone cells in the laminate may be enhanced by the addition of certain mononuclear cell populations or by the addition of growth factors to the culture medium.

The device has utility in vitro to produce biological products in high yield. For example, a differentiated cell which, in the presence of the substrate, produces large quantities of a particular biological product could be grown using the device and the product can be trapped and isolated within the laminate material (e.g., extracellular matrix, cell-surface-associated products). Differentiated cells which produce more soluble products (e.g. growth factors, regulatory factors, peptides, hormones, etc.), can also be grown. In particular, if the transformed cell excretes the product directly into the laminate matrix or the nutrient medium, the product can be isolated from the laminate into the nutrient medium, the product may be readily isolated from the laminate or medium using standard separation techniques (e.g., HPLC, column chromatography, electrophoretic techniques, to name but a few). A "bioreactor" could be therefore devised which would take advantage of a continuous flow method for feeding the laminate in vitro for the production of, for example, extracellular matrix or cell-surface-associated products of target cells.

A kit for in vitro studies will comprise the laminate of the invention having a substrate disposed within the chamber, the substrate specific for growing and/or differentiating cells of interest; cells of interest seeded on the laminate; and reagents for determining the effects of a given compound on growth and/or differentiation of the cells of interest. Preferably, the laminate is a collagen matrix and the substrate is DBP.

In another embodiment, the above kit can comprise a collagen laminate lacking substrate and cells. The laminate can be sold freeze-dried or frozen. The kit can comprise the substrate in a separate container for disposition into the chamber of the laminate at an appropriate time. The kit can further comprise one or more reagents for determining the effect of a compound on cells of interest.

An Example of the invention is described in the section below. For purposes of description only, and not by way of limitation, the laminate of the invention is described based upon DBP as substrate and fibroblasts as cells induced by the substrate. It is expressly understood that the device can be used with other types of cells and substrates.

EXAMPLE 1

Chondroinduction of Fibroblasts

MATERIALS AND METHODS

Initial preparation of mold/support material

Medical grade TYGON® tubing (mfg. by Norton, Akron, Ohio) of inner diameter 3/8" and thickness 3/32" is cut into 1 cm lengths. The pieces are washed with cell-culture grade soap in a sonicator, then rinsed with tap water and distilled water. The pieces are packaged and autoclaved at 121 degrees C., 1 kg/cm$^2$ pressure for 10 minutes. To form a mold, one side of the tubing is glued to a 60 mm culture dish with medical grade silicon glue. The mold and dish are dried for 12 hr in sterile hood.

Composite demineralized bone/collagen matrices:

Type 1 soluble collagen solution, for example, CEL-LAGEN® (Cat. #Pc-5-ICN Biomedicals, Calif.), was used for the laminate construction. This consists of purified insoluble type 1 collagen extracted from calf dermis that has been solubilized by pepsin treatment in order to neutralize this collagen solution. About 1/100 of the final volume of 1M HEPES [pH 7.4 (final 10 mM)] and the same volume of 1M NaHCO$_3$ (final 10 mM) were added to the collagen solution. Next, about 120 microliters of 0.5% collagen solution (ICN Biomedicals, IL) was poured into the mold and frozen at −20° C. The concentration of collagen can vary since porosity of the final matrix is a function of the collagen concentrations. A 0.5% pepsin-digested collagen solution which is ph 3 in acetic acid is most preferred. The concentration, however, can be greater than 0.5%, although concentrations much less than 0.3% will not yield a strong enough collagen matrix. Next, a wet folded piece of paper was placed on the top surface of the frozen collagen, but allowing a small, uncovered edge of the laminate to remain exposed.

After freezing, an additional 130 microliters of ice-cold collagen solution was poured over the frozen collagen and frozen again. Finally, a wet tissue was placed on the added frozen collagen to avoid the formation of a dense collagen shell over the laminate. After lyophilization, the tissues were carefully removed from the collagen. Both sides of the laminate were irradiated by UV light for three hours. Approximately 10 mg of DBP was inserted between layers of the collagen laminate and the outer periphery of the layers was secured to a support with placement of silicon flanges above and below the peripheral surfaces of the laminate (See, for example, FIG. 3).

Demineralized bone powder (DBP) was prepared according to standard protocols. Briefly, mammalian bones, for example diaphyseal bones from cows, are stripped of muscle and fat, cleaned of periosteum, demarrowed by pressure and cold water, and dried and fragmented by crushing and pulverizing in a large mill. Care is taken to prevent heating by using liquid nitrogen. The pulverized bone is milled to a particle size between about 75–250 microns. The bone powder is then demineralized with 20 volumes of 0.5N HCl at 4 C. for about 24 hours. The acid is removed every eight hours and fresh acid is added. The powder is then washed with a large volume of water until the wash solution has a neutral pH. The demineralized bone powder is further extracted with three volumes of chloroform and methanol (3:1). The particulate bone is washed with one volume of absolute ethanol and dehydrated with one volume of anhydrous ether.

The DBP is rendered inactive by dissociate extraction with 20 volumes of 4M guanidine-HCl. The solid material is then washed with water, washed with one volume of absolute ethanol and dehydrated with one volume of anhydrous ether.

Cell culture: Human dermal fibroblasts were isolated by explant culture in DMEM with 10% FBS and antibiotics. Human costal chondrocytes (used as positive controls) were isolated by collagenase digestion and cultured in Ham's F-12 with 10% FBS and antibiotics. Bovine articular chondrocytes were also used as a positive control. About $1\times10^6$ target cells were introduced into the open end of the support and allowed to contact the laminate on its upper peripheral surface. In others, cells were inoculated directly into the laminate. After overnight incubation, the laminates were cultured in the molds in a vertical position for achieving effective nutrient exchange. After 3 days, the laminates were removed from the mold and the laminates only were subsequently incubated. Media were changed twice weekly. On days 7 or 10, laminates were harvested and fixed in 2% paraformaldehyde, as described below.

Analysis: For assessment of in vivo activity, laminates with/without DBP or guanidine-extracted DBP residue were deposited in subcutaneous pockets in 28-day-old rats. Laminates were harvested at intervals, fixed in 2% paraformaldehyde, and embedded in glycol methacrylate (JB-4) or paraffin. A series of twenty-micron sections were stained with toluidine blue, enabling visualization of metachromatic matrix around cells. The twenty-micron sections were blocked with 5% normal goat serum and stained with various amounts (1:100 to 1:1000 dilution) of monoclonal antibodies against chondroitin sulfate: CS-56 (ICN Biomedicals, Cat. #63-650-1) or D type (MO-225: Seikagaku America, Cat. #270802), anti-type II collagen (Chemicon Co., Cat. #MAB1330), keratan sulfate (Seikagaku, CatN #270786), anti-proteoglycan (ΔDi-0S: Seikagaku, Cat. #270788), ΔDi-6S: Seikagaku, Cat. #270789), and ΔDi-4S:Seikagaku, Cat. #270790) after chondroitinase ABC digestion. For visualization, the silver-enhanced immunogold procedure was used (AuroProbe LM R, Janssen Biotech NV, Belgium).

RESULTS

In vivo: At intervals, reactive tissue was harvested for histological analysis. DBP laminates prepared as described were not inflammatory, permitted substantial vascularization, provided a scaffold for cellular migration, and induced endochondral osteogenesis.

In vitro: In samples in which fibroblasts were inoculated into the chamber of the laminate in contact with the DBP substrate, viability was good until day 7 but, thereafter, degenerative cells predominated. It is believed that these cells underwent $pO_2$ changes during the transfer that rendered them not viable. Best results were achieved when fibroblasts were seeded on top of the laminate and allowed to migrate through the collagen matrix.

In chondrocyte-bearing laminates, cells infiltrated the collagen network and attached to both DBP and DBP residue. By day 3, metachromatic granular deposits surrounded chondrocytes with immunohistochemical reactivity with cartilage-specific antibodies. In fibroblast-bearing laminates, migration and viability were equivalent with DBP and DBP residue. Fibroblasts were attached to the collagen network and to the particles with evidence of ECM synthesis. Metachromasia and immunoreactivity with cartilage-specific antibodies were not seen around fibroblasts on the collagen laminate nor on the DBP residue. In contrast, fibroblasts in close approximation with DBP were surrounded by metachromatic, immunoreative matrix, similar to that around bonafide chondrocytes.

Anti-keratan sulfate antibodies showed intense staining in and around human chondrocytes attached to the laminate and between DBP particles. Cartilage-specific antibodies were reactive with human fibroblasts on DBP. Also, antibody to chondroitin-4 sulfate was positive for cells on DBP and negative for cells on guanidine-extracted DBP or collagen alone.

CONCLUSIONS

Human dermal fibroblasts expressed chondrocytic properties when cultured in DBP/collagen laminates of the invention. This 3-dimensional in vitro system optimized cellular infiltration. Cells within the laminates were viable for at least 2 weeks. Packing geometry for DBP more closely mimicked the in vivo microenvironment. Cartilage-like matrix was synthesized by dermal fibroblasts near DBP. This system will valuable to define 1) the cell biology of transdifferentiation by osteoinductive material, 2) the influence of other extracellular components (e.g. hyaluronic acid) and soluble factors (e.g. PDGF, TGF-beta) on differentiation, 3) an in vitro biassay of other inductive factors, and 4) the development of composite substitutes for skeletal reconstruction.

EQUIVALENTS

While specific designs have been shown in the preferred embodiments, the invention is not intended to limited by these specific designs. It should be understood that the foregoing description of the invention is intended merely to be illustrative and other embodiments, modifications and equivalents thereof may be apparent to those skilled in the art without departing from the scope or spirit of the invention.

We claim:

1. A device for use in inducing cell differentiation comprising:

wall means, said wall means having an interior surface and an exterior surface, said interior surface defining a chamber, said exterior surface for being placed in contact with biological tissues, said wall means having opening means in communication with said chamber for receiving an induction material and for closing said chamber to contain said induction material, said wall means comprising a biologically compatible, cell-permeable material capable of receiving cells capable of differentiation, said device for containing an induction material in a biological environment, receiving cells in said chamber and allowing said cells to differentiate in the presence of said induction material.

2. The device of claim 1 wherein said wall means and opening means comprise a first wall section and a second wall section, said first wall section defining said chamber area for receiving an induction material and a peripheral edge area, said second wall section having a cooperating peripheral edge area capable of being received by said peripheral edge area of said first wall section to form said chamber.

3. The device of claim 2 further comprising a support engaging the peripheral edge areas of said first and second wall sections to provide closure of said peripheral edge areas and to facilitate handling.

4. The device of claim 3 wherein said support comprises a housing, said housing having an inner surface and an outer surface, said inner surface defining a cavity and having wall retaining means for engaging said wall means.

5. The device of claim 4 wherein said wall retaining means comprises a groove in the inner surface of said housing, said groove engaging the peripheral edge areas of said first and second wall section.

6. The device of claim 5 wherein said inner surface has two cooperating flanges projecting inwardly in spaced relationship to define said groove.

7. The device of claim 4 wherein said housing has two ends, at least one of said ends having planar edge to allow said housing to stably rest on flat surfaces.

8. The device of claim 4 wherein said housing has two ends, at least one of said ends having opening means extending from said outer surface to said inner surface to allow said cavity to be in fluid communication with the environment at said outer surface when said housing is resting on said planar edge.

9. A device for inducing cell differentiation comprising
wall means, said wall means having an interior surface and an exterior surface, said interior surface defining a chamber, said exterior surface for being placed in contact with a biological tissue, said wall means comprising a biologically compatible permeable material capable of receiving cells capable of differentiating to allow such cells to enter said chamber; and,
induction material, said induction material capable of causing a cell to differentiate, said induction material contained in said chamber to allow said device to be placed with biological tissue to make cells differentiated by the induction material within the chamber.

10. The device of claim 9 further comprising at least one cell capable of being induced or having been induced by said induction material, said cell positioned at a location selected from the group of locations extending from the exterior surface of said wall means to a location within said induction material.

11. A device for inducing cell differentiation comprising:
a) wall means, said wall means comprising a biologically compatible structural material and defining a vessel having a chamber for holding an induction material, said wall means having at least one interior surface and at least one exterior surface having a consistent density, devoid of a shell of dense structural material, said interior surface and said exterior surface permeable to cells, said exterior surface for receiving cells capable of differentiation and said interior surface for allowing said cells to enter said chamber; and,
b) induction material, said induction material capable of causing a cell to differentiate, said induction material contained in said chamber, to allow said device to be placed within a subject or placed in communication with nutrient media to make differentiated cells.

12. A device for use in inducing cell differentiation comprising:
a wall means, said wall means comprising a cell-permeable biologically compatible structural material and defining a vessel having a chamber for holding an induction material, said structural material having density, said wall means having at least one interior surface and at least one exterior surface which have a consistent density, devoid of a shell of dense material, said interior surface and exterior surface permeable to cells, said exterior surface for receiving cells capable of differentiation and said interior surface for allowing one or more cells to enter said chamber, said chamber for containing an induction material, said induction material capable of causing a cell to differentiate, to allow the device to be placed within a subject or placed with nutrient media in the presence of cells capable of differentiation to make differentiated cells.

13. The device of claim 12 wherein said wall means comprises a laminate comprising a first layer and a second layer at least one layer having an interior surface and an exterior surface having a consistent density, devoid of a shell of dense structural material, said interior surface and exterior surface permeable to cells, said first layer having a peripheral edge and said second layer having a peripheral edge which edges are engaged to form said chamber.

14. The device of claim 13 wherein said chamber contains an induction material which induction material is without visually apparent void spaces.

15. The device of claim 13, wherein said laminate is biocompatible with respect to said induction material.

16. The device of claim 13 wherein said edges are engaged to form a seam.

17. The device of claim 13 further comprising a support, said support engaging said edges of said first and second layers for holding said vessel.

18. The device of claim 17 wherein said support comprises an annular collar having two opposed ends, said collar having an exterior surface and an interior surface, said interior surface engaging said edges of said first and second layers for holding said vessel.

19. The device of claim 18 wherein said interior surface of such collar and said wall means define a receptacle for receiving one or more cells capable of being induced by said induction material.

20. The device of claim 19 wherein one of said opposed ends has at least one conduit extending from the exterior peripheral surface of said collar to the interior peripheral surface of said collar.

21. The device of claim 20, wherein said conduits are disposed adjacent to said end of said collar.

22. The device of claim 18 wherein said interior surface has a groove which groove engages said edges of said first and second layers for holding said vessel.

23. The device of claim 22 wherein said groove is defined by a first and a second flange, said first and second flange in a facing relationship on the interior surface of said collar to engage said edges of said layers.

24. The device of claim 13, produced by:
providing a first amount of structural matrix material; disposing a first spacer on said structural matrix material; providing a second amount of structural matrix material to said first spacer; disposing a second spacer on said second amount of structural matrix material;

lyophilizing said spacers and structural matrix material; and removing said spacers from said lyophilized matrix to produce a laminate having interior surfaces engaged together in facing relationship to define a substantially hollow chamber that is substantially free of the structural matrix material, and having a lyophilized structural matrix material of a consistent density, said spacers preventing the formation of an impermeable shell.

25. The device of claim 24, wherein said first and second amounts of structural matrix material are provided into a mold comprising a tube having opposed ends.

26. The device of claim 12 wherein said at least one exterior surface and said at least one interior surface comprise UV irradiated protein.

27. The device of claim 12 further comprising an induction material disposed within said chamber, said induction material having inducing activity towards one or more cells that come in contact with said exterior surface.

28. The device of claim 27, produced by:

providing a first amount of structural matrix material; disposing a first spacer on said structural matrix material; providing a second amount of structural matrix material to said first spacer; disposing a second spacer on said second amount of structural matrix material; lyophilizing said spacers and structural matrix material; removing said spacers from said lyophilized matrix to produce a laminate having interior surfaces engaged together in facing relationship to define a substantially hollow chamber that is substantially free of the structural matrix material; and disposing a induction material into said chamber.

29. The device of claim 28, wherein said induction material is demineralized bone powder and said structural matrix material comprises collagen.

30. The device of claim 12 further comprises a support, said support engaging said wall means for holding said vessel.

31. The device of claim 12 wherein said structural material comprises a structural protein matrix.

32. The device of claim 31 wherein said induction material comprises an osteogenic material.

33. The device of claim 32 wherein said osteogenic material comprises demineralized bone powder.

34. The device of claim 31, wherein said structural protein comprises collagen.

35. A device for use in inducing cell differentiation comprising:

a biologically compatible cell-permeable, matrix defining a chamber, said matrix being a laminate including a first and second layers of a permeable structural matrix, each of said layers having an interior and exterior peripheral surfaces, said interior peripheral surfaces of said interior and exterior layers engaged together in facing relationship, defining said chamber therebetween; and an induction material contained in said chamber for causing a cell to differentiate.

36. The device of claim 35 further comprising the cell contained within said chamber.

* * * * *